United States Patent
Greppi et al.

(10) Patent No.: US 6,561,982 B2
(45) Date of Patent: May 13, 2003

(54) METHOD AND APPARATUS FOR ULTRASOUND IMAGING IN THE PRESENCE OF CONTRAST AGENTS, PARTICULARLY IN THE FIELD OF CARDIOLOGY

(75) Inventors: Barbara Greppi, Florence (IT); Marino Cerofolini, Arezzo (IT)

(73) Assignee: Esaote, S.p.A., Monferrato (IT)

( * ) Notice: Subject to any disclaimer, the term of this patent is extended or adjusted under 35 U.S.C. 154(b) by 0 days.

(21) Appl. No.: 09/900,610

(22) Filed: Jul. 6, 2001

(65) Prior Publication Data

US 2002/0004634 A1 Jan. 10, 2002

(30) Foreign Application Priority Data

Jul. 6, 2000 (IT) .......................................... SV20A0029

(51) Int. Cl.[7] .............................. A61B 8/14; A61B 8/00
(52) U.S. Cl. ....................... 600/458; 600/437; 600/443
(58) Field of Search ................................ 600/458, 443, 600/437

(56) References Cited

U.S. PATENT DOCUMENTS

| 5,415,171 A | | 5/1995 | Goh et al. ............. 128/660.07 |
| 5,694,937 A | | 12/1997 | Kamiyama ............. 128/661.01 |
| 5,735,281 A | | 4/1998 | Rafter et al. ........... 128/660.01 |
| 5,848,968 A | * | 12/1998 | Takeuchi .................... 600/458 |
| 5,957,845 A | | 9/1999 | Holley et al. ............... 600/440 |
| 6,056,691 A | * | 5/2000 | Urbano et al. .............. 600/443 |
| 6,110,120 A | * | 8/2000 | Holley et al. ............... 600/458 |
| 6,171,246 B1 | * | 1/2001 | Averkiou et al. ........... 600/458 |

FOREIGN PATENT DOCUMENTS

| WO | 99/08599 | 2/1999 | ............ A61B/8/00 |
| WO | 00/30541 | 6/2000 | ............ A61B/8/00 |

OTHER PUBLICATIONS

"Dobutamine Stress Echocardiography Identifies Hybernating Myocardium and Predicts recovery of Left Ventricular Function After Coronary Revascularisation", by Cigarros et al. from "Circulation", vol. 88, No. 2 of Aug. 1993.

"Left Ventricle II: Quantification of sequential Dysfunction" and "Left ventricle III coronary Artery Disease–Clinical Manifestations and complications", Clinical Applications pp. 629 through 645 and pp. 677 through 681.

* cited by examiner

*Primary Examiner*—Marvin M. Lateef
*Assistant Examiner*—Ruby Jain
(74) *Attorney, Agent, or Firm*—Woodard, Emhardt, Naughton, Moriarty & McNett LLP

(57) ABSTRACT

A method for ultrasound imaging in the presence of contrast agents, particularly in the field of cardiology, including detecting physiological, especially electrocardiographic signals; transforming the signals or a part thereof into pulses for controlling an ultrasonic probe pointed to the heart region, to synchronize it with the heart cycle; performing image acquisitions at predetermined heart cycle phases for predetermined limited times, with a predetermined ultrasonic beam intensity; processing the received signals and displaying them on a display. Image acquisition takes place in the systolic phase of each heart cycle from the end of diastole to the end of systole, a certain fixed number of acquisitions per unit time and an intensity of the ultrasonic beams being determined with the help of an intermediate Mechanical Index for controlled destruction of a certain percentage of contrast agent microbubbles.

19 Claims, 4 Drawing Sheets

METHOD AND APPARATUS FOR ULTRASOUND IMAGING IN THE PRESENCE OF CONTRAST AGENTS, PARTICULARLY IN THE FIELD OF CARDIOLOGY

REFERENCE TO RELATED APPLICATION

The present patent application claims foreign priority benefits under 35 U.S.C. §119 to Italian patent application No. SV2000A000029, filed Jul. 6, 2000, now pending.

BACKGROUND OF THE INVENTION

The invention relates to a method for ultrasound imaging in the presence of contrast agents, particularly in the field of cardiology, including the following steps:

detecting physiological, especially electrocardiographic signals (ECG);

transforming said signals or a part thereof into pulses for controlling the activation of an ultrasonic probe pointed to the heart region, to synchronize scanning and echo signal acquisition with the heart cycle;

performing image acquisitions at predetermined phases of the heart cycle for predetermined limited times, with a predetermined ultrasonic beam intensity (I);

processing the received signals and transforming them into control signals which are viewable on a display.

A problem involved in the use of contrast agents consists in the need to limit ultrasonic pulse intensity to avoid destruction or damaging of contrast agent microbubbles.

Such intensity limitation has the side effect of decreasing the signal-to-noise ratio, thereby affecting image quality which is particularly important particularly in cardiology for assessment of ventricular wall motion.

Intensity reduction also generates problems in that reflected signals produced by contrast agent microbubbles have a typical frequency which is of the order of harmonics of the fundamental frequency of the ultrasonic beams transmitted to the body under examination, particularly of the second harmonic. Obviously, the amplitude of the second harmonic signal is lower, as compared with the one having the fundamental frequency whereby, in order to achieve sufficient intensities of second harmonic reflected signals, the power of the ultrasonic beams emitted by the probe shall normally be increased. If the intensity of second harmonic or higher-order harmonic reflected echoes is not sufficient, the fundamental frequency reflected signal, related to more echogenic tissues is similar to or higher than the second harmonic reflected signal related to contrast agents, whereby these echo signals from contrast agents can no longer be detected, the probe being somehow "dazzled" by fundamental frequency signals.

In order to obviate this drawback, several different scan protocols are known which allow to limit microbubble destruction to a certain predetermined amount.

According to U.S. Pat. No. 5,735,281, the control signal provided by an electrocardiogram is used to identify the heart cycle phase during which scanning is to be performed. In this document, at the beginning of each heart cycle phase, an image (referred to as image frame) is acquired by using high or full intensity ultrasonic scan beams, and this first image acquisition is followed, within the predetermined phase of each heart cycle, by a succession of image acquisitions with low intensity ultrasonic beams referred to as locator frames.

These subsequent low intensity scans/image acquisitions are used to form a real-time image only allowing to make sure that the probe is properly positioned. Due to the above reasons, image acquisitions which use low intensity ultrasonic beams do not allow to detect useful second harmonic signals, and for instance the presence of contrast agents in the object region, i.e. the coincidence of the scan with the presence of contrast agents in the object region cannot be detected. Contrast agents take a certain time before spreading in the object region.

According to the above mentioned document, the high or full intensity acquisition beam is repeatedly transmitted in every heart cycle at different times or phases of the cycle, which are defined on the basis of a predetermined variation rule, which may be also a statistically random rule. Images acquired at a high intensity are processed and displayed after acquisition. Such method does indeed at least limit the destruction of the microbubbles of the contrast agent due to the high mechanic index of the transmitted beam. However the method disclosed teaches to wait for the next heart cycle for acquiring the next image frame. Thus the acquisition of the useful images useful for diagnostic investigation is limited approximately to only a frame for each heart cyclus or to very long time periods between successive image frame acquisitions. This leads to a very low frame rate for the diagnostic useful image frame. The image refresh rate is very low.

Another draw back relates to the fact that only some image frames are taken in considering the physiological meaning of the heart cycle. In fact acquiring different image frames distributed during the entire heart cycles leads to mixing up images taken in different conditions of the blood circulation and may lead to incorrect interpretations of the results.

U.S. Pat. No. 5,957,845 provides a scan/acquisition protocol similar to the previous document, only differing in that the heart cycle phase during which high or full intensity scanning, i.e. image frame acquisitions, and the subsequent low intensity locator frame acquisitions are performed, is identical in each cycle, i.e. has an identical time location and an identical length in each heart cycle. Although this method discloses a multiple image frame acquisition in each heart cycle, according to the disclosure of U.S. Pat. No. 5,957,845, the time delay between the acquisition of high intensity image frames is very long, so that also in this case there is a very low image refresh rate of the diagnostically useful high resolution and quality images. Furthermore also the teaching of U.S. Pat. No. 5,957,845 does not consider the physiological effect on the conditions of circulation of the blood of the different phases of the heart cycle.

Document WO/030541 teaches to acquire only a high intensity image frame for each heart cycle. No particular choice of the time of acquisition of the image frame within the heart frame is made and no reason for the particular choice disclosed is given. The physiological meaning of the heart cycle on the condition of the blood circulation is totally ignored.

The above acquisition methods have serious limits, especially as regards the definition of the image obtained by the transmission of low or limited intensity ultrasonic beams. Reflected signals do not provide real-time images having a high definition, or anyway such a definition as to allow the use thereof for diagnostic purposes, but are only limited to the function of verifying the proper orientation of the probe with respect to the heart.

Moreover, in order to obtain high signal-to-noise ratio images, these methods require long scanning times distributed over a considerable number of heart cycles, to obtain a diagnostically valid image. Therefore they do not allow a real-time display of the ultrasound image derived by reflected echoes of high intensity ultrasonic signals.

A further drawback consists in that the images acquired by low intensity ultrasonic beams are not adapted to generate echoes having a sufficient intensity at the frequency of the second harmonic or of higher-order harmonics. This actually prevents a real-time detection of the presence of contrast agents which, as is known, reflect in a non linear manner, i.e. the echoes produced thereby have frequencies equal to the second harmonic of the fundamental frequency of illuminating ultrasonic beams, or to higher-order harmonics. In these conditions, i.e. with low intensity beam acquisitions, the reflected signal having frequencies equal to the second harmonic, i.e. relating to contrast agents, has a lower intensity as compared to the one having the fundamental frequency and relating to echogenic or hyperechogenic tissues. Therefore, it is apparent that low intensity acquisitions do not allow to verify in real-time and with due certainty that acquisition takes place while contrast agents are present in the object region.

Since images obtained by high or full intensity acquisition cannot be displayed in real-time, and since contrast agents have a short-time permanence in the object regions and/or a short-time activity, it is likely that acquisition has to be repeated, with a new injection of contrast agents, thereby increasing examination invasiveness.

Another drawback is caused by the fact that image acquisition takes place with no particular attention to the characteristics of physiologic implications of the phases of each heart cycle.

Therefore, the invention is based on the need to improve an ultrasound imaging method, which provides no or little destruction of contrast agents and allows a real-time display of an ultrasound image being valid for interpretation/diagnosis, without requiring expensive adaptations or changes to the equipment as compared to prior art methods.

The invention achieves the above purposes by providing a method for ultrasound imaging as described hereinbefore, wherein image acquisition takes place in the systolic phase of each heart cycle from the end of diastole to the end of systole, a certain fixed number of acquisitions per unit time and an intensity of the ultrasonic beams being determined with the help of an intermediate Mechanical Index for controlled destruction of a certain percentage of contrast agent microbubbles.

The duration of the above phase is relatively constant, even with changes of heart frequency and is of about 350 ms.

It has to be underlined that contrary to the state of the art, the present invention takes advantage of the recognition of the physiological meaning of the different phases of the heart cycle and of their characteristics. On the basis of this knowledge the present invention takes a precise choice of the phase of the heart cycle during which the images have to be acquired.

The particular choice of acquiring only during the systolic phase has two important advantages.

The first advantage consists in the fact that the systolic phase is in good approximation equal in any individual. This means that the phase takes place at constant times from the R-peak and that the duration is nearly constant in any individual.

Thus the machine can work with a constant timing for acquisition. Furthermore there is a common basis from the physiological point of view for comparing images relating to different patients, which may help the doctor in carrying out comparative analysis. This advantage is enhanced by the fact that according to the invention the image frames are acquired only during the systolic phase, i.e. always and for every patient in the same physiological conditions for what it concerns the circulation of the blood.

It has also to be stressed out that while the methods according to the state of the art modulates the global energy transmitted to the body and to the contrast agent by modulating the time periods between image acquisition pulses, the method according to the invention modulates the global power transmitted to the body and to the contrast agent by modulating the intensity of each transmitted pulse.

Furthermore it must also be stressed out that with the method according to the invention, several frames in rapid sequence are acquired, during the same systolic phase, i.e. during the same heart cycle.

From the physiological point of view the choice of the systolic phase is advantageous because in this phase the blood flow is increased due to the ventricular contraction and a certain flow of blood may be present and detected also in the microvascular regions which is not the case in other phases of the heart cycle.

Particularly besides image frames also several locator frames may be acquired during the other phases of the heart cycle different from the systolic phase and/or alternatively or in combination also during the systolic phase. The locator frames are acquired by transmitting low power pulses in a similar way as disclosed in the state of the art.

Typically, the intensity of the ultrasonic beams emitted by the probe is in a range having such maximum and minimum values as to provide Mechanical Indexes of 0.2 to 1.0, preferably of 0.3 to 0.6, for example for a ⅔ MHz probe.

The determination of the Mechanical Index for controlled destruction of contrast agent microbubbles may be calibrated based on an experimentally established empirical scale, or these values are known and indicated by the contrast agent supplier.

The intensity or power of the ultrasonic beams may be held constant or varied in a predetermined manner, so that the total delivered power within a whole heart cycle phase during which the predetermined number of image acquisitions is performed is substantially constant and corresponding to an average predetermined value of the intermediate Mechanical Index.

By this arrangement, the intensity of the individual acquisitions may be modulated in accordance with any pattern whatever, for instance within each phase of each heart cycle, with reference to the predetermined number of acquisitions per heart cycle phase.

Advantageously, within a heart cycle phase selected for performing the predetermined number of acquisitions, in order that proper probe positioning may be substantially detected in the first image acquisitions, a certain number of first image acquisitions is performed by using ultrasonic beams whose intensity corresponds to a low Mechanical Index, particularly to the lower limit of the provided intermediate Mechanical Index, the energy which has not been delivered during the first acquisitions is redistributed as a corresponding intensity increase over a certain number of last acquisitions of the number of acquisitions predetermined for the heart cycle phase.

This results in a controlled destruction of contrast agent microbubbles which remains substantially constant within the heart cycle phase during which the successive acquisitions are performed. However, additionally, the first acquisitions using ultrasonic beams whose intensities are equal to or lower than the lower limit of the predetermined range of intensities corresponding to the intermediate Mechanical Index are used to locate the image formed thereby and to assess simultaneity with the presence of contrast agents, whereas the subsequent acquisitions whose intensities are intermediate between the two limits of said range of predetermined intensities corresponding to intermediate Mechanical Indexes and having intensities equal to or higher than said higher limit, are the ones which produce images being actually valid for diagnostic purposes.

Ultrasonic beam intensities over the individual acquisitions of the same phase of the same heart cycle may vary from a predetermined minimum value to a predetermined maximum value and in such a manner as to maintain the total power transmitted onto the contrast agents in the predetermined number of image acquisitions at a constant level, in accordance with distribution and increase rules for the individual acquisitions which may be random, linear or non-linear and anyway selected at will based on specific needs.

In accordance with a further characteristics, if the total mechanical power delivered during the acquisition stage, comprising the predetermined number of individual acquisitions per heart cycle phase is held as a reference constant, then both parameters may be modulated, i.e. the intensity of illuminating ultrasonic beams in each acquisition and the number of acquisitions within each heart cycle phase during which said acquisitions are performed.

Synchronism with the systolic phase of each heart cycle is achieved by acquiring the electrocardiogram and using the R-wave of said cycle. Acquisition takes place within 350 ms after the R-wave, which represent, to a high degree of approximation, the systolic phase.

Systolic phase acquisition is advantageous from the physiological point of view, because in said systolic phase, coronaries having a higher circulatory activity in the microcirculatory system are compressed. This results in an increased dynamism which adds useful information for perfusion detection or monitoring. Conversely, during diastole blood flow is almost essentially present in large vessels.

The acquisition of several images (frames) by using ultrasonic scan beams having such an intensity as to obtain an intermediate Mechanical Index and to determine a controlled destruction of contrast agent microbubbles, allows to harmonize the needs of achieving a sufficient intensity of second harmonic echoes, a high number of acquisitions at said intensity, and a limited destruction of contrast agent microbubbles. The advantages consist in a real-time display of images and in the possibility to remove artifacts thanks to multiple image acquisitions in the same heart cycle phase.

The method of the invention may be also implemented in combination with the so-called stress-echo. Stress echo technique is known in the art and described in its basics, for instance in "Dobutamine Stress Echocardiography Identifies Hybernating Myocardium and Predicts recovery of Left Ventricular Function After Coronary Revascularisation", by Cigarros et al. from "Circulation", Vol. 88, no. 2 of August 1993.

In this case, the heart may imaged when the patient is in both rest and stress conditions, the latter being obtained by motor activity or by pharmacological action.

The method according to the invention may be also provided in combination with any kind of imaging modalities, such as harmonic imaging, 2D and or 3D imaging, color flow, power doppler, doppler tissue colorization, pulse inversion, pulse difference, B-mode imaging and or combinations of two or more of the said listed modalities.

SUMMARY OF THE INVENTION

A method for ultrasound imaging in the presence of contrast agents, particularly in the field of cardiology, according to one embodiment of the present invention includes the steps of detecting physiological signals, transforming the signals into pulses for controlling the activation of an ultrasonic probe, performing image acquisitions at predetermined phases of the heart cycle for predetermined limited times, processing the received signals and transforming those signals into control signals which are viewable on a display wherein the invention is characterized in that image acquisition takes place in the systolic phase of each heart cycle from the end of diastole to the end of systole, a certain fixed number of acquisitions per unit time and an intensity of the ultrasonic beams being determined with the help of an intermediate Mechanical Index for controlled destruction of a certain percentage of contrast agent microbubbles.

One object of the present invention is to provide an improved method and apparatus for ultrasound imaging in the presence of contrast agents.

Related objects and advantages of the present invention will be apparent from the following description.

DESCRIPTION OF THE PREFERRED EMBODIMENT

Figure 1:
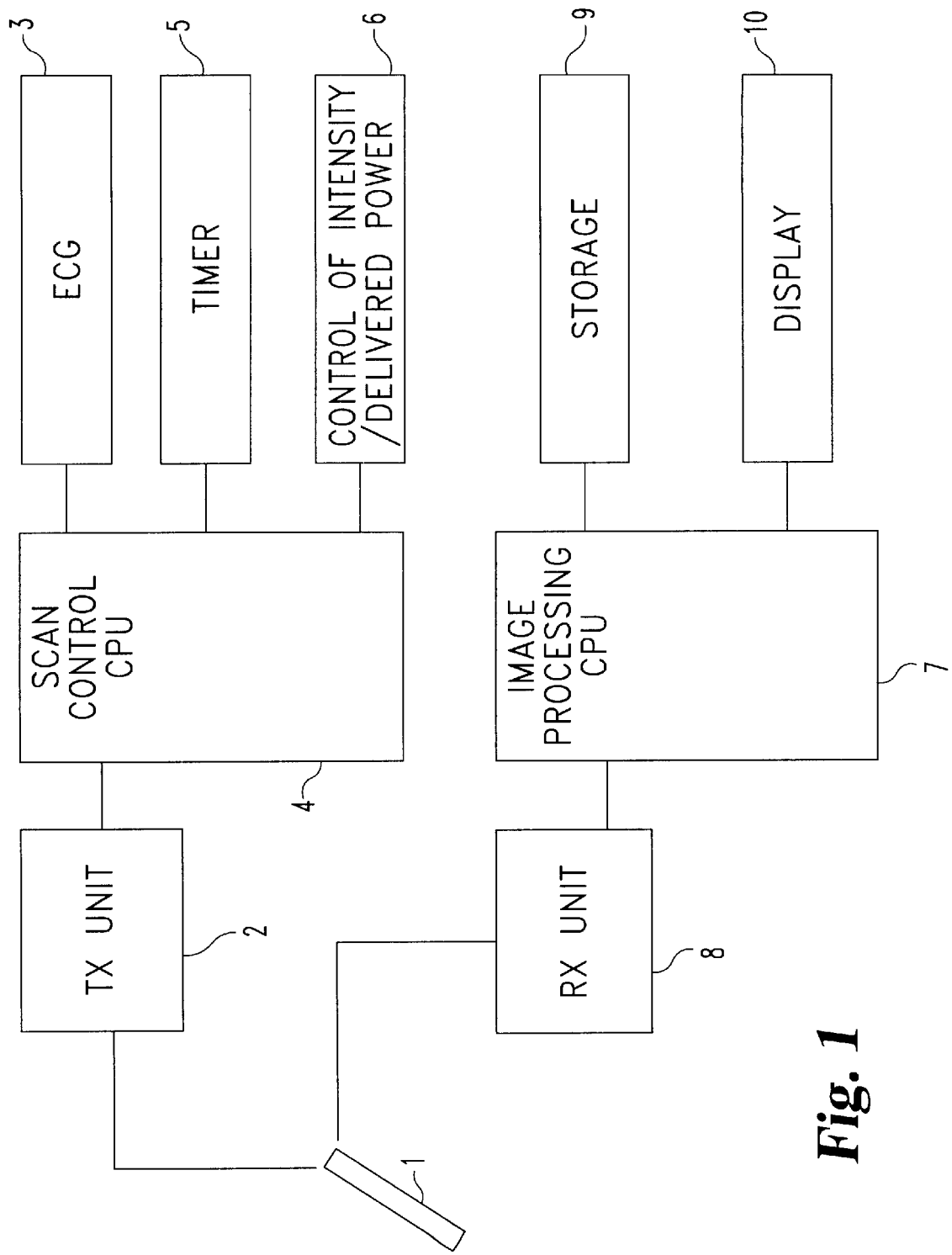
FIG. 1 is a simplified block diagram of an ultrasound apparatus for implementing the method of the invention.

Referring to FIG. 1, an ultrasound apparatus includes a probe 1 having a transducer for emitting ultrasonic beams and for receiving reflected echoes, as well as for transforming them into corresponding signals.

The probe 1, i.e. the transducers, are controlled by an exciting and beamforming unit 2 which is intended to excite the transducers of the probe 1 for transmission and to control focusing of said beams along scan lines, planes and/or volumes, depending on the type of probe in use. The exciting and beamforming unit 2 is controlled by a control unit 4, e.g. a microprocessor which receives output signals from a physiological signal processing unit (ECG) 3 and transforms them, with the help of a timer 5, into control signals for activation and deactivation of the probe 1, i.e. of the exciting and beamforming unit 2. The control unit 4 is also connected to a unit 6 for setting the minimum and maximum intensity values assigned to the ultrasonic beams emitted by the probe 1 and the number of image acquisitions per unit time and for controlling the total power delivered within a predetermined number of successive acquisitions.

These values may be directly set manually, or through conventional setting means, not shown in detail and connected to the unit 6, or may be selected from a plurality of preset combinations by using any type of hardware and software selectors, e.g. even a pop-up menu.

Obviously, the synchronization signal provided by the ECG unit 3 to the control unit 4 is also provided to the RX and processing control unit 7. This unit 7 is also advantageously of the microprocessor type and controls, together with the unit 4, a RX and reconstructing unit denoted by numeral 8, as well as one or more storage units 9 of any type and the displaying media 10, such as a monitor, and/or a printer, and/or the like.

Figure 2:
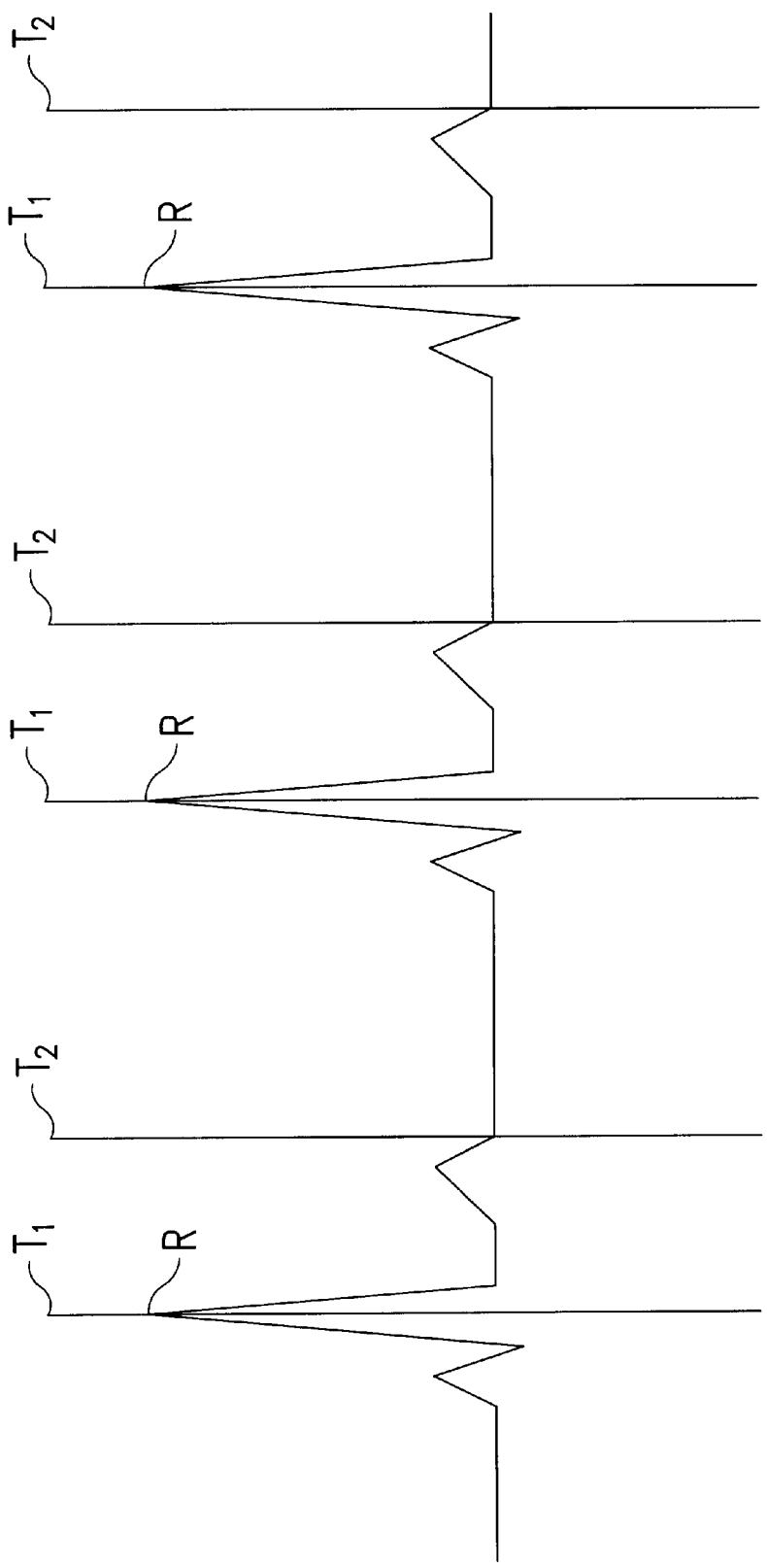
FIG. 2 is a schematic view of an echocardiographic diagram of the heart cycle.

FIG. 2 shows a portion of an electrocardiogram plot wherein the peak of the so-called R-wave is recognizable. Lines T1 and T2 define the time limits of the systolic phase during which successive image acquisitions are performed. The number of image acquisitions n is predetermined and distributed over the duration of the systolic phase T1 to T2, which is of about 350 ms.

The acquisition of images during the systolic phase has a considerable diagnostic relevance, particularly when combined with contrast agents, which, as is known, have the purpose to allow the display of blood flow conditions, with blood being intrinsically non echogenic and allowing little or no displaying thereof with normal ultrasound imaging techniques.

During the systolic phase, coronaries are compressed, which results in an increased circulatory activity in the microcirculatory system. This results in an increased dynamism which adds useful information for perfusion detection or monitoring.

With reference to FIGS. 1 and 2, the invention provides that the control unit 4 is or may be programmed for execution of a number n of image acquisitions within the period of 350 ms after the synchronization pulse corresponding to the R-wave of the electrocardiogram. The intensity of the transmitted ultrasonic beams is controlled by the unit 6 which holds it at a level corresponding to a Mechanical Index intermediate between the maximum allowed value and the minimum useful level.

Particularly, ultrasonic beam intensity is controlled in such a manner that the corresponding Mechanical Index is of 0.3 to 0.6, considering 1.9 as a maximum allowed index for a ⅔ MHz probe.

The unit 4 and the unit 6 may be also programmed in a different manner.

Figure 3:
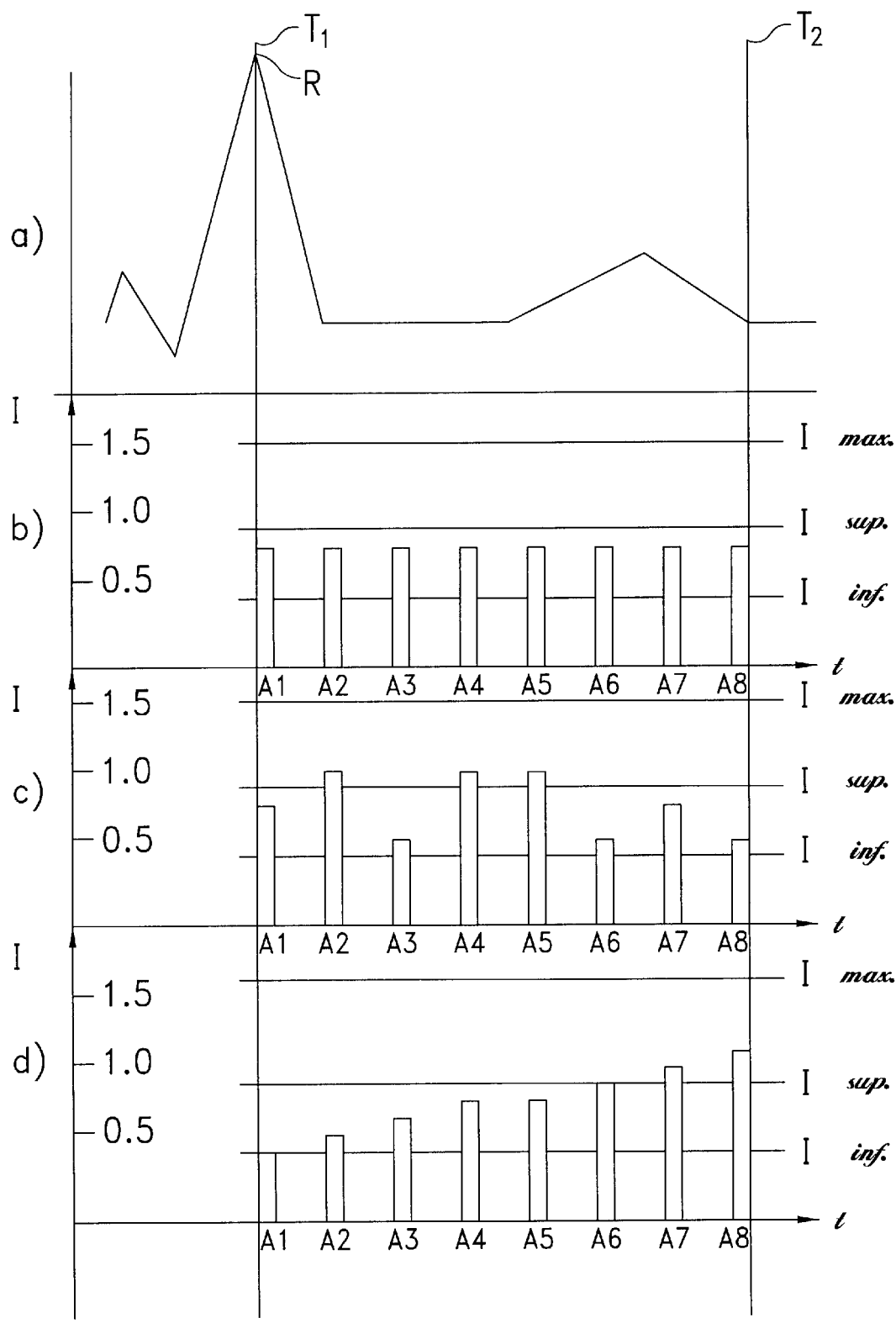
FIGS. 3 and 4 show different examples of image acquisition types according to the invention combined with a heart cycle.
Figure 4:
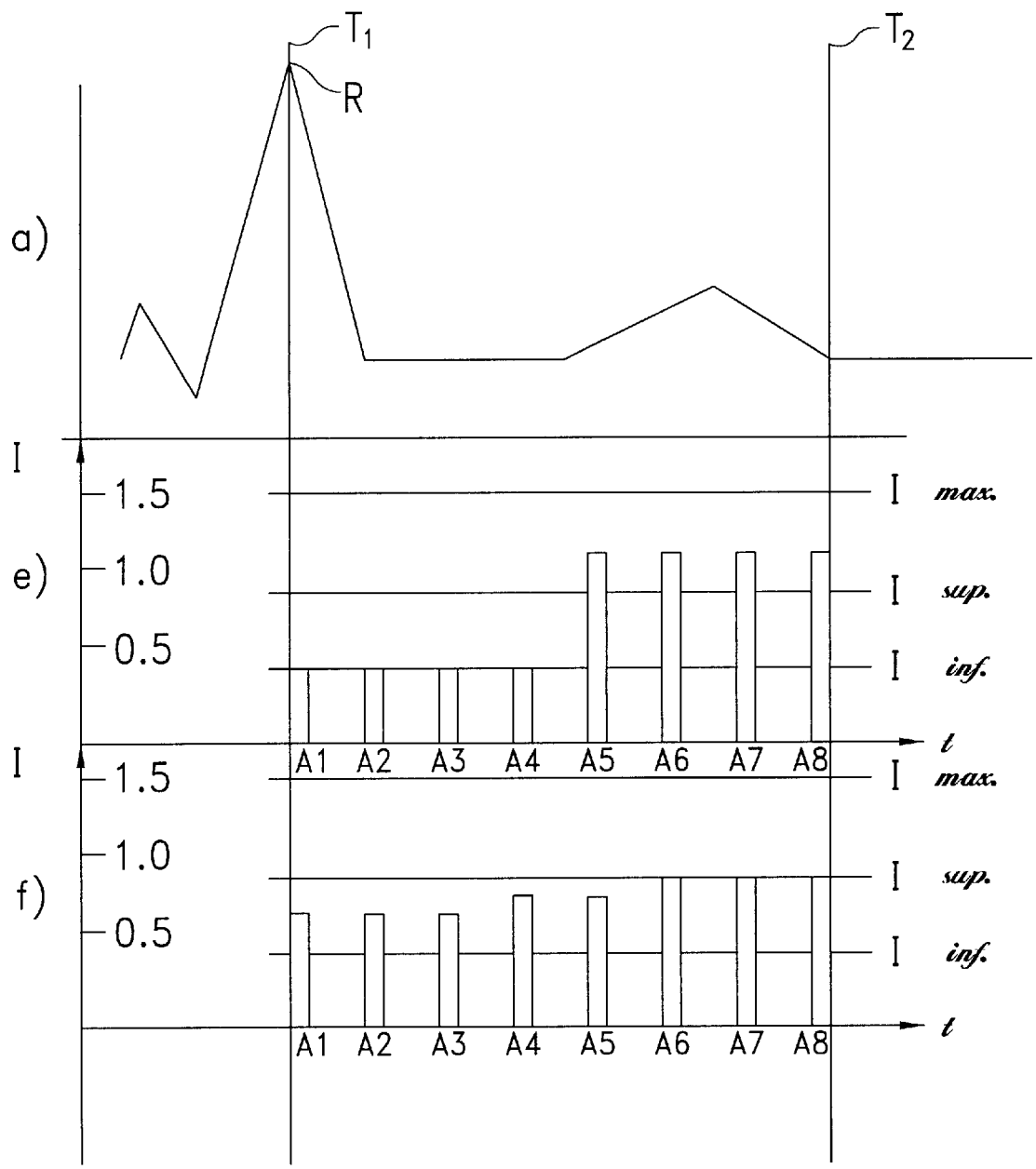

FIGS. 3 and 4 show different modes of performing n successive image acquisitions in the systolic phases.

Graph a) shows an enlarged heart cycle and the two vertical lines T1 and T2 define the start and end times of the systolic phase, during which acquisition is performed.

Graphs b), c), d), e) and f) show different modes of performing the n acquisitions.

The example is only illustrated by way of indication and it can provide no quantitative information, but only principle information.

In this case, 8 image acquisitions are performed in the interval from T1 to T2. The horizontal lines I inf. I sup. show the lower and the upper limit of the range wherein ultrasonic beam intensity corresponds to Mechanical Indexes of 0.3 to 0.6.

I max. shows the maximum allowed intensity value, corresponding to the maximum allowed Mechanical Index.

With reference to graph a), eight acquisitions A1, A2, A3, A4, A5, A6, A7, A8 are performed during the systolic phase (T1, T2), all at the same intensity, which corresponds to an intermediate Mechanical Index, in the range defined by I inf. and I sup. Ultrasonic beams have such an intensity as to cause a predetermined and controlled percentage destruction or degradation of contrast agent microbubbles, which is sufficient to obtain second harmonic echo signals whose degree is acceptable for discriminating them from fundamental echo signals and for displaying diagnostically valid images.

In accordance with a variant embodiment of the method according to the invention, the intensity of ultrasonic beams for each of the n, in this case eight acquisitions may be variable. This variation may be provided in such a manner that in each acquisition the intensities of the relevant ultrasonic beams only change within the predetermined range, extending from I inf. and I sup. or that intensities may also be higher and/or lower than one or both of said limits as defined by I inf. and I sup.

In this case, in order that controlled microbubble destruction may still be provided, it is possible to hold, as constant values, the number of acquisitions n (in this example being without limitation equal to 8) and the total energy delivered over the n image acquisitions, while maintaining the correspondence of said total energy of the n image acquisitions with a predetermined value in said range from I Inf. to I Sup.

The distribution of intensity changes over n acquisitions may be at random, as shown in chart b) of FIG. 3. In this case, the area of each bar of the histogram represents power, whereas height indicates intensity. As is shown, the ultrasonic beam intensity reduction during the acquisitions A3, A6 and A8 is compensated for by a corresponding intensity increase in the acquisitions A2, A4 and A5. The acquisitions A1 and A7 are performed at the predetermined normal intensity, i.e. the one shown in graph a). The total energy, which corresponds to the sum of all the areas of the bars A1 to A8 is the same in all acquisition successions as shown in graphs b) and c).

The graph d) shows a further variant of ultrasonic beam intensity modulation in each acquisition of the n acquisitions performed during the systolic phase.

In this case, the first acquisitions A1 to A3 are performed with increasing intensities starting from the intensity I inf. The acquisitions A4 and A5 are performed at the normal intensity, i.e. at the same level as the acquisition of graph b), whereas the acquisitions A6, A7 and A8 are performed at an intensity which increases in inverse proportion to the lower intensity of the acquisitions A1 and A3 as compared with the intensity being considered as the normal value of the acquisitions A4 and A5. Here again, the total energy delivered to contrast agents is the same as in the n acquisitions of graph b).

Referring now to FIG. 4, graphs e) and f) show a few variants of intensity progression described with reference to the example of graph d).

The difference of the variant as shown in graph e) consists in that the first four acquisitions A1 to A4 are performed with ultrasonic beam intensities of I inf., whereas the other four acquisitions A5 to A8 are performed with a higher intensity as compared with the normal value as defined in graph b), so that ultrasonic beam intensity during acquisitions A5 to A8 is caused to exceed the upper limit I Sup.

Here again the total energy delivered onto contrast agents is the same as in the previous examples of graphs b), c), d), and so is substantially the percentage of destroyed or inactivated microbubbles.

In the example of graph f), the intensity distribution is such that, while the same pattern of lower levels in the first acquisitions is maintained, the last acquisitions do not exceed the upper limit I Sup. Here again the total energy is the same as in the preceding examples.

Obviously, the above examples are to be intended without limitation, since any ultrasonic beam intensity variation or progression rule may be provided in the individual acquisitions of each phase T1–T2. Moreover, the examples always refer to minimum intensities which are never lower than the intensity level I inf. However, intensity distribution patterns may be provided wherein some acquisitions, particularly the first acquisitions have intensities below I Inf.

Intensity distribution according to examples d), e) and f) is particularly advantageous, allowing to obtain a reduced microbubble destruction during the first acquisitions. In this case, the relevant information is the one pertaining to proper probe positioning with respect to the heart or to the organ or body being examined and to assessment of contrast agent presence in the object region. Hence, such an intensity of ultrasonic beams is only required as to obtain reliable information about positioning and about the presence of contrast agents, said information being sufficient to allow discrimination between echoes having second harmonic frequencies and those having the fundamental frequency.

Obviously it is possible to combine the ultrasonic beam intensity variation with a variation of the number n of acquisitions per phase, still with reference to a constant total energy delivered through the n acquisitions.

Ultrasonic beam intensity changes through the individual acquisitions, as well as the change of the acquisition number per heart cycle phase may be provided automatically by the ultrasonic beam intensity controlling unit 6 which, when appropriately programmed, accounts for the changes made and, based on the preset distribution rule, changes the intensities of ultrasonic beams in each acquisition, to maintain the total delivered energy and/or the destruction or inactivation of contrast agent microbubbles associated thereto at a constant level.

Means for continuous variation and adjustment of the parameters I Inf., I. Sup. of the ultrasonic beam intensity distribution rule on the individual acquisitions A1 to An and of the number n of acquisitions per heart cycle may be provided.

Several different types of said parameters may be also programmed, which may be selected by the user by means of hardware selectors, such as switches or the like or by means of software selectors, such as pop-up menus or the like.

The ultrasound apparatus and the method according to the invention may be used in combination with the so-called stress echo technique.

This technique provides ultrasound imaging of the heart, particularly of the left ventricle, while the patient is both in rest and stress conditions. Stress may be induced by physical exercise or by injection of Dobutamine or other drugs.

Stress echo technique is known in the art and described in its basics, for instance in "Dobutamine Stress Echocardiography Identifies Hybernating Myocardium and Predicts recovery of Left Ventricular Function After Coronary Revascularisation", by Cigarros et al. from "Circulation", Vol. 88, no. 2 of August 1993. Other pertinent documents are: "Left Ventricle II: Quantification of sequential Dysfunction" and "Left ventricle III coronary Artery Disease—Clinical Manifestations and complications", Clinical Applications pp. 629 through 645 and pp. 677 through 681.

U.S. Pat. No. 5,415, 171 provides the combination of the use of contrast agents with the stress echo technique.

All these documents, and U.S. Pat. No. 5,415,171 in particular do not allow to perform a stress echo examination substantially in real-time, due to the problems outlined above, i.e. by the destruction of contrast agents at high ultrasonic beam intensities.

However, in combination with the characteristics of the method of the invention, it is possible to first acquire images with contrast agents when the patient is in the normal position, and then to acquire images of the patient in the stress condition and with contrast agents. These images may be displayed individually or sequentially in real-time and, images of the patient in the normal condition may be displayed at the same time, by way of comparison, by recalling them from the memory individually or sequentially.

Real-time perfusion display, thanks to a proper adjustment of ultrasonic beam intensity in the presence of contrast agents allows to visualize phenomena, such as particularly transient ischemia.

The invention is not limited to the embodiments illustrated and described herein, but may be greatly varied. Particularly, changes may be made to the structure of the ultrasound apparatus for implementing the method of the invention, wherein the hardware structure may be greatly varied in accordance with the described features. All the above without departure from the guiding principle disclosed above and claimed below.

What is claimed is:

1. A method for ultrasound imaging of the heart region of a patient in the presence of contrast agents, in the field of cardiology, having the following steps:

detecting physiological signals;

transforming said signals or a part thereof into pulses for controlling activation of an ultrasonic probe pointed to said heart region, to synchronize scanning and echo signal acquisition with said patient's heart cycle;

performing image acquisitions at predetermined phases of said heart cycle for predetermined limited times, with a predetermined ultrasonic beam intensity;

processing the received signals and transforming them into control signals which are viewable on a display;

characterized in that image acquisition takes place exclusively in the systolic phase of each heart cycle from the end of diastole to the end of systole, a certain fixed number of acquisitions per unit time and an intensity of the ultrasonic beams being determined in accordance with a Mechanical Index for controlled destruction of a certain percentage of contrast agent microbubbles.

2. A method according to claim 1, characterised in that the acquisitions carried out in said systolic phase are acquisitions of diagnostically useful image frames.

3. A method according to claim 1 or 2, characterised in that one or more or a sequence of locator frames is also acquired, the acquisition of this locator images being carried out in the phases of the heart cycle different from said systolic phase and/or also during said systolic phase and the pulses transmitted to the body being of low energy, i.e. of low mechanical index relating to the energy needed for destroying the microbubbles of the contrast agents.

4. A method as claimed in claim 1, characterized in that the duration of the acquisition stage is constant and is of about 350 ms, regardless of heart frequency.

5. A method as claimed in claim 1, characterized in that the intensity of the ultrasonic beams emitted by the probe is in a range having such a maximum value and such a minimum value as to provide Mechanical Indexes of 0.2 a to 1.0, preferably of 0.3 a to 0.6, for ⅔ MHz frequencies.

6. A method as claimed in claim 1, characterized in that the determination of intensity corresponding to a Mechanical Index for controlled destruction of contrast agent microbubbles is achieved by an experimentally established empirical scale.

7. A method as claimed in claim 1, characterized in that the intensity or power of the ultrasonic beams may be held constant or varied in a predetermined manner, so that the total delivered power within a whole heart cycle phase during which the predetermined number of image acquisitions is performed is substantially constant and corresponding to a predetermined value of the intermediate Mechanical Index.

8. A method as claimed in claim 1, characterized in that, within each phase of each heart cycle during which acquisition takes place, ultrasonic beam intensity for the individual acquisitions is varied in accordance with a predetermined distribution rule, with reference to the predetermined number of acquisitions per heart cycle phase.

9. A method as claimed in claim 1, characterized in that, within each phase of the heart cycle phase selected for performing the predetermined number of acquisitions, in order that proper positioning of the probe may be substantially detected in the first image acquisitions, a certain number of first image acquisitions is performed by using ultrasonic beams whose intensity corresponds to a low Mechanical Index, particularly to the lower limit of the provided intermediate Mechanical Index, whereas the energy which has not been delivered during said first acquisitions is redistributed as a corresponding intensity increase over a certain number of last acquisitions of the number of acquisitions predetermined for the heart cycle phase.

10. A method as claimed in claim 1, characterized in that ultrasonic beam intensities over the individual acquisitions of the same phase of the same heart cycle may vary from a predetermined minimum value to a predetermined maximum value and in such a manner as to maintain the total power transmitted onto the contrast agents in the predetermined number of image acquisitions at a constant level, in accordance with distribution and increase rules for the individual acquisitions which may be random, linear or non-linear and anyway selected at will based on specific needs.

11. A method as claimed in claim 1, characterized in that, if the total mechanical power delivered during the acquisition stage, comprising the predetermined number of individual acquisitions per heart cycle phase is maintained constant, then both parameters are modulated or varied, i.e. the intensity of ultrasonic beams in each acquisition and the number of acquisitions within each heart cycle phase during which said acquisitions are performed.

12. A method as claimed in claim 1, characterized in that within each phase of each heart cycle, the same intensity is used for the ultrasonic beams of each acquisition.

13. A method as claimed in claim 1, characterized in that two sets of ultrasound images of the heart are acquired in the presence of contrast agents, the first set providing ultrasound images of the heart when the patient is at rest, and the second set providing ultrasound images of the heart in stress conditions obtained by motor activity or pharmacological action.

14. A method as claimed in claim 13, characterized in that the images acquired when the patient is in the stress condition are displayed in real-time either individually or sequentially, while previously acquired ultrasound images of the patient at rest are displayed for comparison therewith.

15. An apparatus for ultrasound imaging in the presence of contrast agents and for implementing the method as claimed in claim 1, characterized in that it includes:
  a probe having transducers for emitting ultrasonic beams and for receiving reflected echoes, as well as for transforming them into corresponding signals;
  a transducer transmission exciting and beamforming unit being used to control focusing of said beams along scan lines, planes and/or volumes;
  means for triggering the probe and the control unit in synchronization with a synchronization signal provided by an external electrocardiograph or an embedded physiological signal processing unit;
  a unit for controlling the reception and image processing of the received echo signals, operating in synchronization with the activation of deactivation of the probe for transmission;
  one or more ultrasound image storage units and displaying media, characterized in that it further includes:
    programmable means for setting the minimum allowed intensity and the maximum allowed intensity for ultrasonic beams emitted by the probe and the number of image acquisitions per unit time.

16. An apparatus as claimed in claim 15, characterized in that it includes programmable and automatic means for controlling the total power delivered over a predetermined number of acquisitions, and for changing ultrasonic beam intensity for each acquisition, while a preset constant is maintained, corresponding to the value of the total power delivered over the whole succession of acquisitions in each phase of each heart cycle.

17. An apparatus as claimed in claim 15, characterized in that the values of ultrasonic beam intensity and of the upper and lower limits of said intensity may be set either directly, manually, or by conventional setting means, or may be selected from a plurality of preset or preprogrammed combinations by using, for instance, any type of hardware and software selectors, e.g. even of the pop-up menu type.

18. An apparatus as claimed in claim 15, characterized in that the means may be programmed according to an ultrasonic beam intensity distribution algorithm over the individual image acquisitions during each phase of each heart cycle.

19. A method according to claim 1, characterized in that it is provided in combination with any kind of imaging modalities, such as harmonic imaging, 2D and or 3D imaging, color flow, power doppler, doppler tissue colorization, pulse inversion, pulse difference, B-mode imaging and or combinations of two or more of the said listed modalities.

* * * * *